United States Patent [19]

Larkin et al.

[11] Patent Number: 4,540,821
[45] Date of Patent: Sep. 10, 1985

[54] AMINOPOLYOLS FROM SUGARS

[75] Inventors: John M. Larkin, Austin; Ernest L. Yeakey, Houston; Lewis W. Watts, Jr., Austin, all of Tex.

[73] Assignee: Texaco Inc., White Plains, N.Y.

[21] Appl. No.: 228,436

[22] Filed: Jan. 26, 1981

[51] Int. Cl.$^3$ .............................................. C07C 85/08
[52] U.S. Cl. .................................... 564/473; 564/471; 564/480
[58] Field of Search ........................ 564/473, 471, 480

[56] References Cited

U.S. PATENT DOCUMENTS 2,830,983  4/1958  Lemieux ......................... 564/473 X
4,021,539  5/1977  Moller et al. ......................... 424/73

FOREIGN PATENT DOCUMENTS 49-27848  7/1974  Japan .................................... 564/473
844448    8/1960  United Kingdom .

OTHER PUBLICATIONS

Long, J. W. and G. N. Bollenback, *Methods of Carbohydrate Chemistry*, R. L. Whistler and M. L. Wolfram, ed., Academic Press: NY, (1963), vol. 2, pp. 79–83.

Tronchet, J. M. J., Bruno Baehler and J. B. Zumwald, *Helv. Chim. Acta,* Geneva: Inst. Chim. Pharm., Univ. Geneva: Geneva, Switz. (1977), 60(6), pp. 1932–1934.

Komoto, M., S. Fujii and H. Tsuchida, *Hyogo Noka Daigaku Kenkyu Hokoku, Nogei-Kagaku Hen,* (1962), vol. 5, pp. 124–128.

Herstein, Karl M., "The Function of a Screening Laboratory, " *Chemical and Engineering News,* Jun. 11, 1956, pp. 2862–2864.

*Primary Examiner*—Charles F. Warren
*Attorney, Agent, or Firm*—Jack H. Park; Kenneth R. Priem

[57] ABSTRACT

A process for the manufacture of aminopolyols and polyaminopolyols by continuous reductive amination of sugars in aqueous solution is described. Syrups such as corn syrups may be used directly for this process. It has been found that the lower the mol ratio of $NH_3$ to the sugar, with a ratio of 1 as the lower limit, the higher is the degree of nitrogen incorporation into the sugar. It is essential that the streams of ammonia and aqueous sugar solution be pumped to the reaction zone separately.

3 Claims, No Drawings

1

AMINOPOLYOLS FROM SUGARS

BACKGROUND OF THE INVENTION

1. Field of the Invention

This invention relates to the production of aminopolyols and polyaminopolyols, and particularly relates to methods of making aminopolyols from corn syrups by continuous reductive amination in which the degree of amination may by increased by reducing the mol ratio of ammonia to sugar.

2. Prior Art

Previously, aminopolyols or polyaminopolyols have been made using homogeneous catalysts. These methods required extensive filtering and catalyst recovery procedures. Further, many of the feedstocks used to make aminopolyols are quite expensive. It is therefore an object of this invention to provide a means for making aminopolyols using an inexpensive feedstock, such as corn syrups, and a heterogeneous catalyst such as a hydrogenation-dehydrogenation nickel catalyst.

A number of other researchers have reductively aminated glucose and other sugars. For example, J. W. Long and G. N. Bollenback in *Methods of Carbohydrate Chemistry* (R. L. Whistler and M. L. Wolfram, ed., Academic Press, N.Y.) Vol. 2, pp. 79–83 (1963) describe how D-glucose in a methanol solution reacted with ammonia over a nickel catalyst to give up water will produce 1-amino-1-deoxy-D-glucitol. A mixture of piperazines, mixtures of amino-alcohols, ethylenediamine, and water are produced over a nickel catalyst by reacting sucrose, cornstarch, Bagasse pith or glucose with $NH_3$, $MeNH_2$, $MeCH_2NH_2$, or $EtNH_2$ along with water and hydrogen as described in British Pat. No. 844,448. U.S. Pat. No. 4,021,539 discloses how monosaccharides or their corresponding uronic acids may be reacted with secondary or tertiary amines over palladium, copper-chromium, and nickel hydrogenation catalysts to produce N-polyhydroxyalkyl-amines which are useful in skin-treating cosmetic compositions.

The reaction of aldehydo or keto sugars with primary or secondary amines and hydrogen over palladium carbon catalysts to produce secondary or tertiary amino sugars is described in Tronchet, J. M. J; B. Baehler, H. B. Zomwald, Helv. Chim. Acta. 1977 60(6), 1932–34. The use of sodium bisulfite to inhibit the browning reaction of glucose and ammonia to make imidazoles has been disclosed in M. Komoto, S. Fujii and H. Tsuchida, Hyogo Noka Daigaku Kenkyu Hokuku, Nogei-Kagaku Hen 5, 124–8 (1962).

SUMMARY OF THE INVENTION

The invention concerns a method for the production of aminopolyols comprising continuously reacting aqueous solutions of sugars with ammonia and hydrogen, the sugar solutions and the ammonia being pumped to the reaction zone in separate streams, the reaction occurring in the presence of a hydrogenation-dehydrogenation catalyst at temperatures in the range from about 50° to about 250° C. and in which the degree of amination may be increased by reducing the mol ratio of ammonia to sugar, with one as the lower limit.

DESCRIPTION OF THE PREFERRED EMBODIMENTS

Generally, the invention involves the production of amino polyols, polyaminopolyols and mixtures thereof by the method of continuous reductive amination of aqueous solutions of sugars with ammonia and hydrogen over a hydrogenation-dehydrogenation catalyst. It was found that the degree of amination could be controlled by the reaction temperature, the space velocity, or the ratio of reactants. An unexpected result was that the lower the mol ratio of ammonia to sugar, with 1 as a lower limit, the higher is the degree of nitrogen incorporation for a given set of conditions. This effect is exactly opposite of that found in the amination of other alcohols, aldehydes, or ketones. It was also discovered that it is much preferred to pump the ammonia to the reaction zone in a stream separate from the aqueous sugar solution to avoid plugging of the reactor lines.

The sugars in aqueous solution used as reactants are preferably aldose sugars, including sugars containing a substantial amount, from 5 to 100%, of disaccharides and higher saccharides. It is especially preferred that the aqueous sugar solutions be corn syrups because they are inexpensive and are a renewable resource.

The syrups useful in this invention preferably contain from 5 to 98% water with the balance being such sugars as glucose, maltose, maltotriose, and higher saccharides, for example. Solutions both rich and poor in glucose content have been shown to be useful as reactants in the method of this invention. It should be emphasized that the invention would work with other types of syrups.

Any hydrogenation-dehydrogenation type catalyst which can be tableted fo fixed bed operation, and which will remain stable in service would be suitable for the method of this invention. The examples herein demonstrate that cobalt and nickel catalysts give excellent results. A more complete description of the nickel and cobalt catalysts used in the examples are given in U.S. Pat. No. 3,152,998, which is incorporated herein by reference. The basic components of these catalysts are nickel, copper and chromium oxide or cobalt, copper and chromium oxide in various proportions.

The reaction is preferably conducted in the temperature range from about 50° to about 250° C. It is especially preferred that the reaction temperature be in the range from about 100° to about 225° C. As will be seen in the examples, the degree of amination increases with increasing temperature. If a very active catalyst is employed, such as palladium, lower temperatures should be used to achieve the same degree of amination obtained with a less active catalyst at higher temperatures. Similarly, the pressure range for this method may run from about 50 to about 6000 psig, depending on the activity of the catalyst.

As noted earlier, the degree of amination or nitrogen incorporation may be controlled by varying the temperature, the space velocity, or the reactant ratio. While the degree of amination increases with increasing temperature, it decreases with increasing reactant space velocity. Typical liquid hourly space velocities may run from about 0.5 g liquid/ml catalyst/hour or less to 10 g liquid/ml catalyst/hour or greater. Nitrogen incorporation also decreases with an increasing mol ratio of ammonia to sugar. These trends can be seen by examination of Example V.

Roughly speaking, a $NH_3$/sugar mol ratio of greater than 30 results in the production of monoaminopolyols, while a mol ratio of less than about 30 produces mostly polyaminopolyols. Temperature and space velocity values both affect this rough boundary value. Of course, it is difficult to control this amination precisely, and what usually results as a product is a mixture of monoaminopolyol and polyaminopolyol. Mixtures of mono- and polyamino polyols have a number of uses which are described below.

The characteristics and advantages of the method of this invention discussed up to now are illustrated by the following examples.

EXAMPLE I

Ten kg of Royal ® Glucose Liquid 2626 (29% $H_2O$, 71% sugars of which glucose comprises 92%, maltose comprises 4%, and maltotriose and higher saccharides comprises 4%) diluted with 3.333 kg $H_2O$ was pumped at 0.42 lb/hr and anhydrous $NH_3$ was pumped in a separate stream at 1.36 lb/hr to 475 cc of nickel hydrogenation-dehydrogenation catalyst contained in a 500 ml continuous tubular reactor. All of the commercial sugar products used in these examples were obtained from Corn Products Company, a division of CPC International Inc. The catalyst was manufactured by Harshaw Chemical Co. and is further described in U.S. Pat. No. 3,152,978, as are all the catalysts of these examples. Hydrogen was fed to the reactor at 105 liter/hr and reactor pressure was maintained at 2500 psig. Operation was conducted thus for three hours pre-run and four hours on-stream at each of the following temperatures: 130°, 140°, 160°, 175°, 190° C. All on-stream products were filtered and vacuum-stripped at 79° to 81° C. at 35 to 55 mm Hg. Products were all clear liquids. Analytical and other data follow.

| Operating Temp., °C. | Weight (g) product | Total amine meq/g | Total Acetylatables meq/g | Percent Nitrogen | Secondary and Tertiary Amines meq/g | Per-Cent $H_2O$ |
|---|---|---|---|---|---|---|
| 130 | 498.5 | 4.45 | 24.4 | 6.17 | 0.047 | 22.7 |
| 140 | 477.7 | 5.81 | 11.2 | 8.2 | 0.148 | 17.6 |
| 160 | 388.7 | 8.94 | 24.4 | 12.7 | 1.32 | 13.3 |
| 175 | 350.5 | 11.1 | 22.3 | 15.9 | 2.55 | 16.3 |
| 190 | 243.3 | 14.7 | 20.4 | 21.0 | 4.75 | 7.4 |

Inspection of the data indicates that total amines total nitrogen content, and secondary and tertiary amine content all increase as function of temperature, but that total replaceable hydrogens (as measured by acetylatables) and amount of $H_2O$ retained on stripping decrease with temperature.

The product made at 130° C. solidified after standing at room temperature. A portion was recrystallized from aqueous ethanol. The IR and NMR spectra and nitrogen analysis were consistent with a monoaminopentahydroxyhexane.

EXAMPLE II

The procedure of Example I was essentially duplicated with the following differences: Globe ® Corn Syrup 1634, 18% $H_2O$, 82% sugars (43% dextrose, 32% maltose, 8% maltotriose, and 17% higher saccharides), replaced the glucose solution, and dilution of $H_2O$ was 7.5 kg to 7.5 kg corn syrup. Also, $H_2$ flow was 70 liter/hr and operating temperatures were 140°, 155°, 170°, 185°, 200°, 210°, and 220° C. Products were stripped at 78° to 80° C. at 26 to 35 mm Hg. Analytical data follows.

| Operating Temp., °C. | Total Amine, meq/g | Total Acetylatables, meq/g | % Nitrogen | Sec. and Tertiary Amines, meq/g | % $H_2O$ |
|---|---|---|---|---|---|
| 140 | 5.42 | 25.2 | 8.4 | 0.522 | 6.32 |
| 155 | 7.47 | 24.9 | 10.7 | 0.015 | 6.93 |
| 170 | 9.45 | 23.9 | 13.7 | <0.01 | 4.05 |
| 185 | 12.4 | 20.7 | 18.0 | 3.65 | 2.38 |
| 200 | 13.4 | 17.1 | 20.3 | 1.95 | 1.85 |
| 210 | 13.2 | 13.9 | 21.9 | 4.47 | 2.09 |
| 220 | 12.6 | 10.8 | 22.6 | 0.58 | 2.25 |

EXAMPLE III

The corn syrup of Example II was mixed with 1600 g of $H_2O$ and 1200 g of anhydrous $NH_3$. The very dark brown solution was pumped at 24 ml/hr to a 25-cc continuous tubular reactor filled with nickel catalyst tablets together with 6 liters/hr of a 3:1 molar ratio $H_2/N_2$ with reactor pressure at 2500 psig. The reactor was pre-run for 3 to 4 hours followed by 20 to 21 hours product collection at each of the following temperatures: 160°, 175°, 190° C. Reactor actually only operated for 10 minutes collection time at 190° C. because of plugging of the reactor lines.

EXAMPLE IV

The corn syrup of Example II was mixed with 2000 g of reagent grade concentrated aqueous $NH_4OH$ solution and 800 g of $NH_3$. Procedure of Example III essentially repeated (at 170°, 185°, and 210° C.) with essentially the same result; i.e., only a short time on stream at the highest temperature before reactor plugged. Analyses follow of samples stripped at 98° C./42 min.

| Operating Temp., °C. | Total Amine, meq/g | Total Acetyl atables, meq/g | % Nitrogen | Sec. & Tertiary Amines, meq/g |
|---|---|---|---|---|
| 170 | 6.02 | 12.5 | 13.8 | 5.04 |
| 185 | 6.49 | 10.8 | 15.3 | 5.25 |
| 210 | 7.05 | 13.5 | 16.4 | 1.88 |

Examples III and IV indicate the preferability of pumping the sugar solution separately from the ammonia.

EXAMPLE V

The equipment, catalyst, and essential procedure of Example I was used under a variety of conditions of temperature, mol ratio $NH_3$/glucose, and total liquid hourly space velocity. The results are tabulated below. It can be noted that as the mol ratio of $NH_3$/glucose decreases the amount of nitrogen incorporation into the product amine increases (except in the extreme case, ratio = 1.1, where $NH_3$ is the limiting reagent) at a given set of temperature/LHSV conditions. In some cases, direct comparisons are not possible from the table but interpolation between temperatures and between LHSV's leads to the same conclusion.

| Mol Ratio $NH_3$/ Glucose | Operating Temp., °C. | (Anhydrous Basis) % Nitrogen | Total Amine meq/g | % $H_2O$ Dilution of Royal Glucose Liq 2626 | LHSV g liq/ml cat/hr |
|---|---|---|---|---|---|
| 60 | 130 | 7.98 | 5.8 | 33 | 1.72 |

-continued

| Mol Ratio NH₃/ Glucose | Operating Temp., °C. | % Nitrogen | (Anhydrous Basis) Total Amine meq/g | % H₂O Dilution of Royal Glucose Liq 2626 | LHSV g liq/ml cat/hr |
| --- | --- | --- | --- | --- | --- |
| 60 | 140 | 9.84 | 7.05 | 33 | 1.72 |
| 60 | 160 | 14.65 | 10.31 | 33 | 1.72 |
| 60 | 165 | 19.0 | 13.03 | 33 | 1.72 |
| 5 | 125 | 11.53 | 6.49 | 41 | 2.0 |
| 5 | 135 | 16.62 | 7.30 | 41 | 2.0 |
| 5 | 145 | 18.44 | 7.22 | 41 | 2.0 |
| 5 | 155 | 20.33 | 7.81 | 41 | 2.0 |
| 10 | 125 | 14.65 | 5.29 | 41 | 2.5 |
| 10 | 145 | 19.76 | 7.77 | 41 | 2.5 |
| 5 | 145 | 17.99 | 6.12 | 41 | 4.0 |
| 27 | 125 | 8.88 | 6.01 | 33 | 2.25 |
| 27 | 135 | 12.02 | 8.00 | 33 | 2.25 |
| 27 | 150 | 14.1 | 9.43 | 33 | 2.25 |
| 27 | 165 | 16.81 | 10.95 | 33 | 2.25 |
| 1.1 | 140 | 8.40 | 3.66 | 33 | 1.7 |
| 1.1 | 165 | 9.0 | 3.96 | 33 | 1.7 |
| 10 | 115 | 11.74 | 5.33 | 41 | 2.5 |
| 10 | 120 | 14.32 | 4.14 | 41 | 2.14 |
| 30 | 165 | 22.6 | 10.31 | 41 | 2.25 |
| 30 | 125 | 13.6 | 5.96 | 41 | 2.25 |

EXAMPLE VI

The procedure of Example I was followed with the following modifications: 4.1 kg H₂O used; glucose solution and NH₃ feed rates were 1.70 and 0.92 lb/hr, respectively; hydrogen flow was 200 liter/hr; temperatures were 120°, 135°, and 150° C.; a cobalt catalyst replaced the nickel catalyst. Analytical data follows:

| Operating Temp., °C. | Total Amine, meq/g | Sec. and Tert. Amine, meq/g | Total Acetylatables, meq/g | % Nitrogen | % H₂O |
| --- | --- | --- | --- | --- | --- |
| 120 | 4.85 | 1.46 | 21.0 | 10.71 | 12.6 |
| 135 | 6.26 | 3.52 | 16.65 | 13.2 | 15.1 |
| 150 | 7.02 | 3.29 | 12.85 | 17.5 | 12.1 |

After 72 hours of service, the used catalyst was in poor condition with approximately 10% fine particles and broken tablets.

EXAMPLE VII

Example II was repeated with some minor modifications. During vacuum stripping, the overhead from runs conducted at 180° to 220° C. was fractionated so that the lighter H₂O was discarded, and the heavier boiling overhead (e.g. 50° to 90° C. bath temperature from 30 to 35 mm Hg) was analyzed for its amines content. Ethylenediamine, ethanolamine, piperazine, 2-methylpiperazine, and suspected morpholine were identified.

Aminopolyols are suitable for a wide variety of end uses. For example, some of the aminopolyols produced by the method of this invention have been used to make successful polyurethane rigid foams. One of the advantages of this inventive process is that filtering and catalyst recovery procedures are unnecessary since the method uses a heterogeneous catalyst. Small amounts of the catalyst have been found to dissolve in the aminopolyol product which do not impede processing but which can cause an accelerating effect for catalyzing polyurethane foams. Other uses for these aminopolyols are lube oil dispersants, artificial sweeteners as described in U.S. Pat. No. 3,549,616, and textile softening agent formulations disclosed in German Offenlegungschrifft No. 1,816,279.

Many modifications and improvements may be made on the method of this invention without departing from the spirit and scope of this invention which is defined only by the appended claims.

We claim:

1. A method for controlling the degree of amination in the continuous production of a mixture of aminopolyols containing primarily polyamino polyols comprising
    (a) pumping an aqueous solution of sugars and ammonia to a reaction zone in separate streams,
    (b) continously reacting the aqueous solution of sugars with ammonia in the presence of hydrogen and a hydrogenation-dehydrogenation catalyst and
    (c) controlling the degree of amination of the resulting aminopolyols by
        (1) increasing or decreasing the reaction temperature between 150° and 250° C. to increase or decrease the degree of amination respectively,
        (2) decreasing or increasing the space velocity of the reaction mass to increase or decrease the degree of amination respectively, and
        (3) decreasing or increasing the mole ratio of ammonia to sugars between 30 and 1 to increase or decrease the degree of amination respectively.

2. The method of claim 1 in which the aqueous sugar solutions consist of corn syrups.

3. The method of claim 1 in which the hydrogenation-dehydrogenation catalyst contains nickel.

* * * * *